(12) United States Patent
Al Barakati et al.

(10) Patent No.: US 10,070,942 B1
(45) Date of Patent: Sep. 11, 2018

(54) ORTHODONTIC CINCH BACK INSTRUMENT

(71) Applicant: KING SAUD UNIVERSITY, Riyadh (SA)

(72) Inventors: Sahar Faisal Al Barakati, Riyadh (SA); Bader Khalid Al Balkhi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/811,320

(22) Filed: Nov. 13, 2017

(51) Int. Cl.
  *A61C 7/14* (2006.01)
  *A61C 7/28* (2006.01)
  *A61C 7/02* (2006.01)
  *A61C 7/30* (2006.01)
  *A61C 7/04* (2006.01)

(52) U.S. Cl.
  CPC .............. *A61C 7/146* (2013.01); *A61C 7/026* (2013.01); *A61C 7/282* (2013.01); *A61C 7/04* (2013.01); *A61C 7/306* (2013.01)

(58) Field of Classification Search
  CPC ........... A61C 5/60; A61C 7/026; A61C 7/146; A61C 7/025; A61C 7/282; A61C 7/04; A61C 7/306
  See application file for complete search history.

(56) References Cited

U.S. PATENT DOCUMENTS

| | | | | |
|---|---|---|---|---|
| 1,676,715 A | * | 7/1928 | Snyder | A61C 3/08 433/163 |
| D241,647 S | | 9/1976 | Ruggieri | |
| 4,167,063 A | * | 9/1979 | Sosnay | A61C 7/02 433/3 |
| 4,472,137 A | * | 9/1984 | Barone | A61C 7/306 433/3 |
| 4,836,781 A | * | 6/1989 | Meinershagen | A61C 5/85 433/141 |
| 5,242,302 A | * | 9/1993 | Riehm | A61C 3/08 433/164 |
| 5,395,236 A | | 3/1995 | Khouri | |
| 6,186,786 B1 | * | 2/2001 | Trushkowsky | A61C 3/08 433/141 |
| D687,553 S | * | 8/2013 | Coreil | D24/149 |

(Continued)

FOREIGN PATENT DOCUMENTS

GB 2451460 A 2/2009

*Primary Examiner* — Nicholas Lucchesi
(74) *Attorney, Agent, or Firm* — Richard C. Litman

(57) ABSTRACT

The orthodontic cinch back instrument is an orthodontic tool used for cinching back an end of an orthodontic wire. The orthodontic cinch back instrument includes an elongated handle portion which extends along a longitudinal axis and has opposed first and second ends. First and second shank portions are respectively secured to, and extend longitudinally from, the first and second ends of the elongated handle portion. First and second arcuate head supports are respectively secured to, and extend from, the first and second shank portions. The first and second arcuate head supports are positioned and contoured antisymmetrically with respect to one another about a lateral axis. First and second heads are respectively secured to the first and second arcuate head supports and are positioned and angled antisymmetrically with respect to one another about the lateral axis. Each of the first and second heads has a slot formed therein.

7 Claims, 4 Drawing Sheets

(56) References Cited

U.S. PATENT DOCUMENTS

| | | | |
|---|---|---|---|
| 9,872,742 B1* | 1/2018 | Albarakati | A61C 7/026 |
| 2006/0063123 A1* | 3/2006 | Cleary | A61C 7/02 |
| | | | 433/3 |
| 2006/0121405 A1* | 6/2006 | Hollard | A61C 7/02 |
| | | | 433/3 |
| 2009/0286199 A1* | 11/2009 | Creasman | A61C 3/00 |
| | | | 433/141 |
| 2012/0107770 A1 | 5/2012 | Beach | |
| 2013/0137058 A1* | 5/2013 | Wong | A61C 19/004 |
| | | | 433/29 |
| 2014/0113246 A1* | 4/2014 | Jaramillo | A61C 3/00 |
| | | | 433/102 |
| 2017/0128157 A1* | 5/2017 | Muller | A61C 3/08 |

* cited by examiner

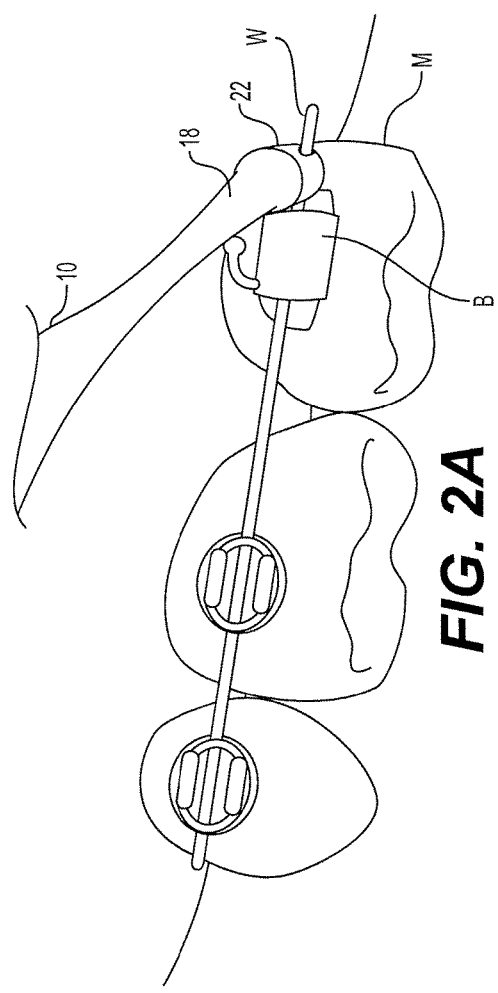
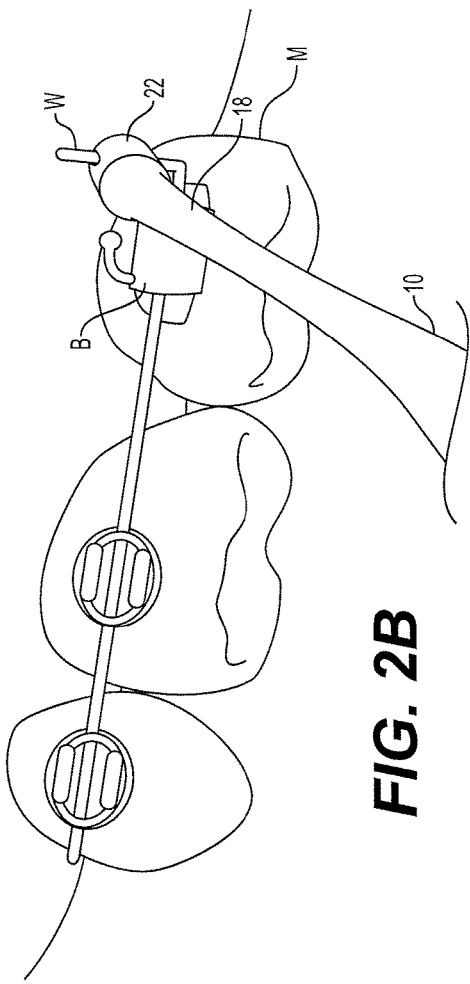
FIG. 2A
FIG. 2B

ORTHODONTIC CINCH BACK INSTRUMENT

BACKGROUND

1. Field

The disclosure of the present patent application relates to orthodontics, and particularly to an orthodontic cinch back instrument for cinching back an end of an orthodontic wire, such as those typically associated with wire braces.

2. Description of the Related Art

In conventional wire braces, an orthodontist typically must make distal cinch back bends of the arch wire for loop activation or securing of arch wires. Large and small diameter arch wires are seated through buccal tubes, which are positioned on the outside of molar bands (positioned on upper or lower molars of the patient). After the arch wire has been secured in place, any excess arch wire projecting distally to the molar tube is cut on both sides. Typically, about 3 mm of wire is left to project through the buccal tube.

In order for the orthodontist to be able to cinch back the remaining wire, the patient is asked to open his or her mouth slightly to facilitate accommodation of the cinching instrument in the buccal vestibule. This slight opening of the mouth is important because opening wide brings the anterior border of the mandibular ramus forward and blocks buccal vestibular accessibility to the molar tubes. Some patients must close their teeth in order to gain better buccal vestibular accessibility. Due to the small available space, as well as the small size of the wire being cinched, it is relatively difficult to cinch such a wire using conventional instruments, such as pliers, orthodontic ligature directors and the like. Thus, an orthodontic cinch back instrument solving the aforementioned problems is desired.

SUMMARY

The orthodontic cinch back instrument is an orthodontic tool used for cinching back an end of an orthodontic wire, such as those typically associated with wire braces. The orthodontic cinch back instrument includes an elongated handle portion which extends along a longitudinal axis and has opposed first and second ends. First and second shank portions are respectively secured to, and extend longitudinally from, the first and second ends of the elongated handle portion. With respect to a lateral axis which is orthogonal to the longitudinal axis and bisects the elongated handle, the first and second shank portions are symmetric with respect to one another about the lateral axis, and the elongated handle is symmetric about the lateral axis. A central portion of the elongated handle may be, for example, cylindrical in overall contour, and first and second opposed end portions of the elongated handle may each be frusto-conical in overall contour.

First and second arcuate head supports are respectively secured to, and extend from, the first and second shank portions. The first and second arcuate head supports are positioned and contoured antisymmetrically with respect to one another about the lateral axis. Preferably, each of the first and second arcuate head supports has a substantially S-shaped contour.

First and second heads are respectively secured to the first and second arcuate head supports. The first and second heads are positioned and angled antisymmetrically with respect to one another about the lateral axis. Each of the first and second heads preferably has a cylindrical contour, with an outwardly facing circular face. The antisymmetric positioning of the first and second heads, and their respective first and second arcuate head supports, provides for the first and second heads to be facing in opposed lateral directions with respect to one another. Each of the first and second heads has a slot formed therein adapted for releasably receiving the end of the orthodontic wire to be cinched back. Preferably, each slot is angled with respect to the longitudinal axis.

These and other features of the present invention will become readily apparent upon further review of the following specification.

BRIEF DESCRIPTION OF THE DRAWINGS

FIGS. 2A and 2B are sequential environmental, perspective views of the orthodontic cinch back instrument in use to cinch back an end of an orthodontic wire.

Similar reference characters denote corresponding features consistently throughout the attached drawings.

DETAILED DESCRIPTION OF THE PREFERRED EMBODIMENTS

Figure 1:
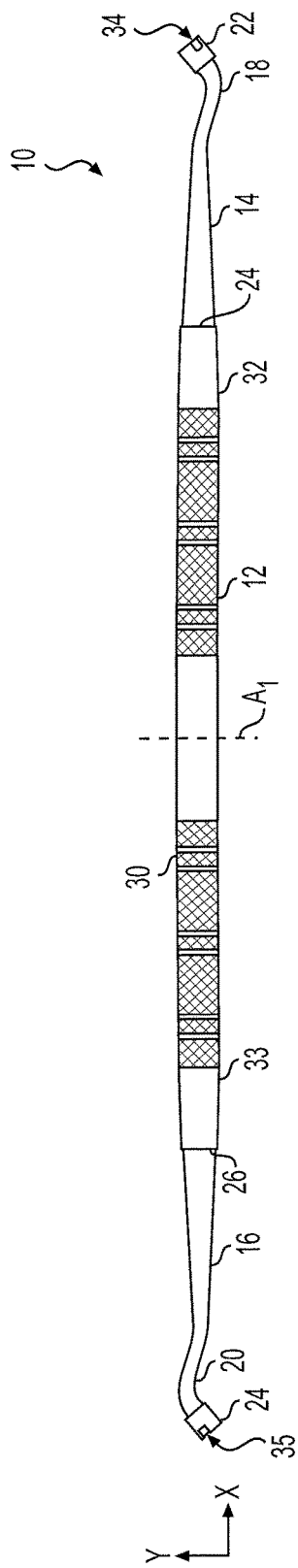
FIG. 1 is a side view of an orthodontic cinch back instrument.
Figure 3:
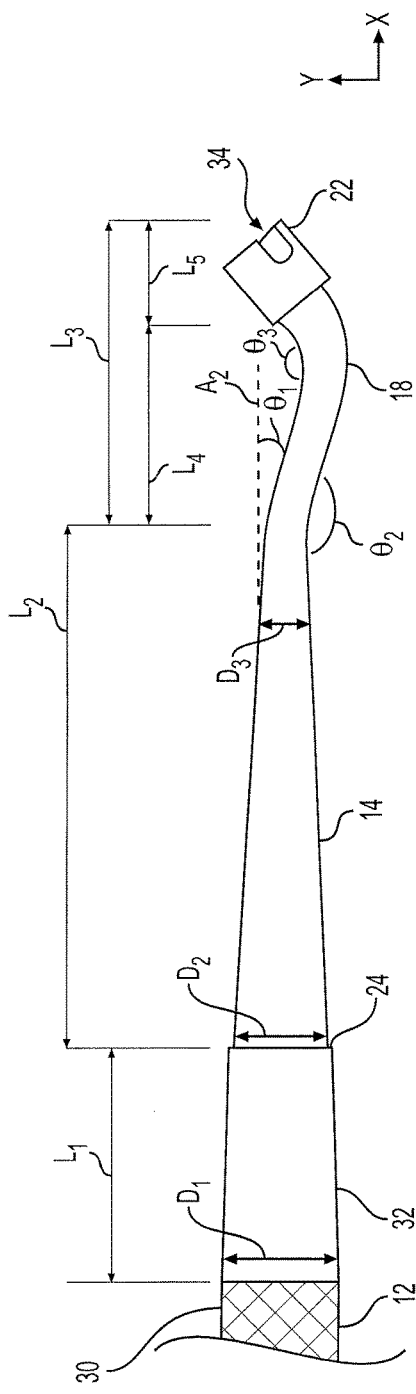
FIG. 3 is a partial side view of the orthodontic cinch back instrument.

The orthodontic cinch back instrument 10 is an orthodontic tool used for cinching back an end of an orthodontic wire, such as those typically associated with wire braces. As best shown in FIGS. 1 and 3, the orthodontic cinch back instrument 10 includes an elongated handle portion 12 which extends along a longitudinal axis $A_2$ and has opposed first and second ends 24, 26, respectively. First and second shank portions 14, 16 are respectively secured to, and extend longitudinally from, the first and second ends 24, 26 of the elongated handle portion 12. With respect to a lateral axis $A_1$, which is orthogonal to the longitudinal axis $A_2$ and bisects the elongated handle 12, the first and second shank portions 14, 16 are symmetric with respect to one another about the lateral axis $A_1$, and the elongated handle 12 is also symmetric about the lateral axis $A_1$. A central portion 30 of the elongated handle 12 may be, for example, cylindrical in overall contour, and first and second opposed end portions 32, 33, respectively, of the elongated handle 12 may each be frusto-conical in overall contour, as shown. In FIGS. 1 and 3, the lateral axis $A_1$ corresponds to the y-direction, and the longitudinal axis $A_2$ corresponds to the x-direction.

As an example, central portion 30 may be cylindrical with a diameter $D_1$ of 4.5 mm. Noting that the first and second opposed end portions 32, 33 are symmetric about the lateral axis $A_1$ and referring to FIG. 3, the smaller diameter end of first end portion 32 may have a diameter $D_2$ of 4.0 mm. For these exemplary dimensions, first end portion 32 may have a longitudinal length $L_1$ of 10 mm. Further corresponding to these exemplary dimensions, first shank portion 14 may have a length of 20 mm, with its diameter tapering from diameter $D_2$ of 4.0 mm to a smaller diameter $D_3$ of 2.0 mm. The orthodontic cinch back instrument 10 may be made from any suitable type of material, such as stainless steel, nickel-titanium alloy or the like. As shown, one or more portions of the elongated handle portion 12 may be textured for gripping.

First and second arcuate head supports 18, 20 are respectively secured to, and extend from, the first and second shank portions 14, 16. The first and second arcuate head supports 18, 20 are positioned and contoured antisymmetrically with respect to one another about the lateral axis $A_1$ such that the directions of their curvature is inverted, with respect to one another, about the lateral axis $A_1$. Preferably, as shown, each of the first and second arcuate head supports 18, 20 has a substantially S-shaped contour. As shown in FIG. 3, corresponding to the exemplary dimensions given above, first arcuate head support 18 may extend longitudinally a distance $L_4$ of 10 mm. As noted above, each of the arcuate head supports is substantially S-shaped in contour. At the juncture of first arcuate head support 18 with first shank portion 14, there is an upper angle of curvature $\theta_1$, with respect to the longitudinal axis $A_2$, of approximately 45°, and a lower angle of curvature $\theta_2$ of approximately 160°. Here, the term "upper" refers to the orientation of the orthodontic cinch back instrument 10 as it is shown in FIG. 3; i.e., the upper angle of curvature $\theta_1$ is laterally above the lower angle of curvature $\theta_2$ in this orientation. With this orientation, at the juncture of first arcuate head support 18 with first shank portion 14, the first arcuate head support 18 is angled generally downwardly with respect to the lateral axis $A_1$. At a second point of curvature, the first arcuate head support 18 angles generally upwardly with respect to the lateral axis $A_1$. Corresponding to the above exemplary dimensions, angle of curvature $\theta_3$, as shown in FIG. 3, may be approximately 120°.

Figure 4:
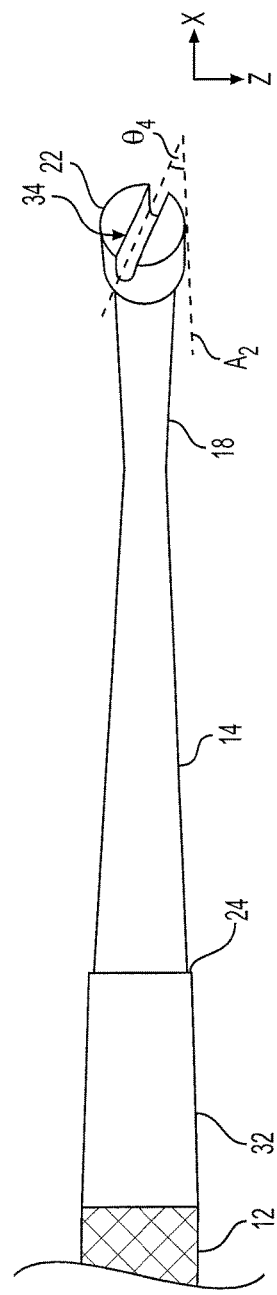
FIG. 4 is a partial bottom view of the orthodontic cinch back instrument.
Figure 5:
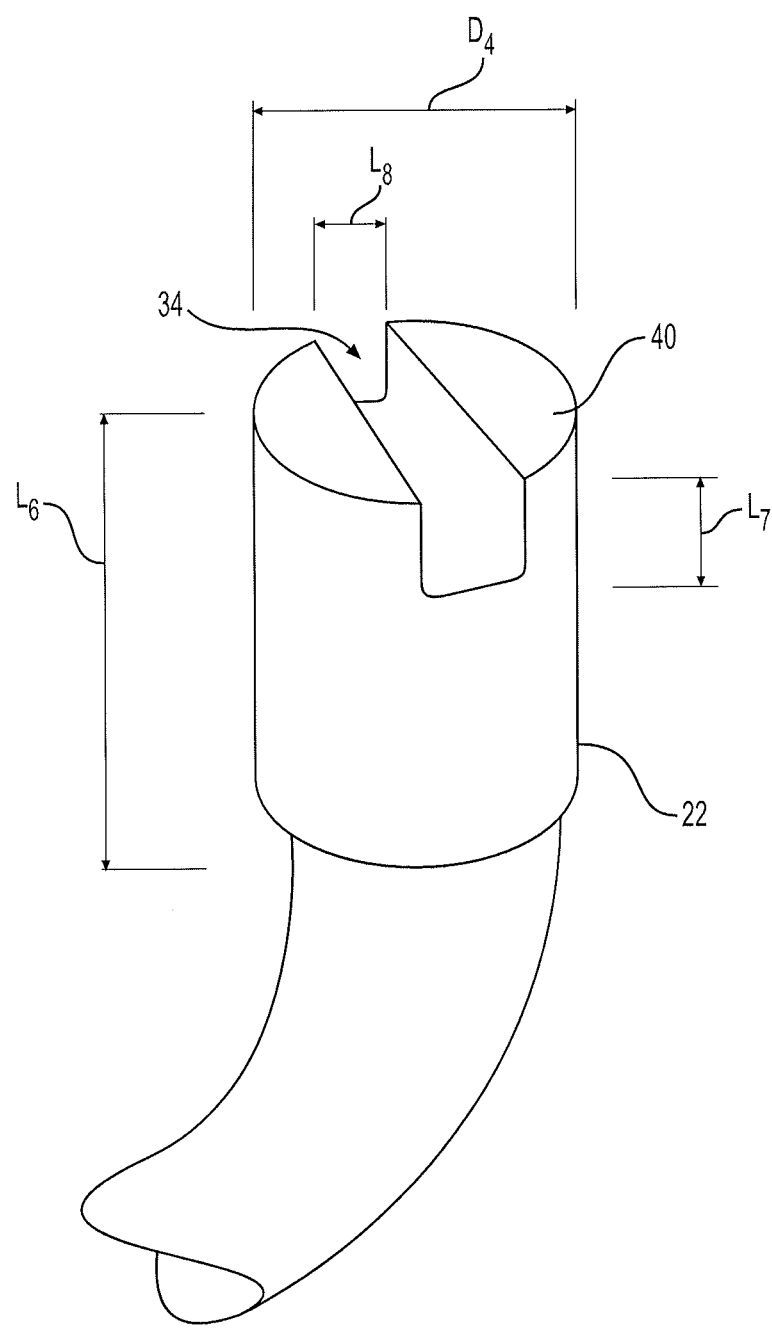
FIG. 5 is a partial perspective view of the orthodontic cinch back instrument.

First and second heads 22, 24 are respectively secured to the first and second arcuate head supports 18, 20. The first and second heads 22, 24 are positioned and angled antisymmetrically with respect to one another about the lateral axis $A_1$. As best shown in FIGS. 4 and 5, each of the first and second heads 22, 24 preferably has a cylindrical contour, with an outwardly facing circular surface 40. The antisymmetric positioning of the first and second heads 22, 24, and their respective first and second arcuate head supports 18, 20, provides for the first and second heads 22, 24 to be facing in opposed lateral directions with respect to one another. Each of the first and second heads 22, 24 has a respective slot 34, 35 formed therein. Preferably, each slot 34, 35 is angled with respect to the longitudinal axis $A_2$. In an embodiment, first head 22 can be used to cinch back the wire extending at the right upper and left lower molar tube and the second end 24 can be used to cinch back the wire extending at the left upper and right lower molar tube. Corresponding to the above exemplary dimensions, as shown in FIG. 3, first head 22 may extend along longitudinal axis $A_2$ a distance $L_5$ of 5 mm, thus giving the combined span of first arcuate head support 18 and first head 22 a longitudinal length $L_3$ of 15 mm. As shown in FIG. 4, an exemplary angle $\theta_4$ of slot 34 formed in first head 22 with respect to the longitudinal axis $L_2$ is approximately 45°. The orientation of FIG. 4 shows rotation of the orthodontic cinch back instrument 10 by 90° about the longitudinal axis $A_2$. In FIG. 4, the z-axis is orthogonal to both the x-axis (represented by longitudinal axis $A_2$) and the y-axis (represented by lateral axis $A_1$).

As shown in FIG. 2A, each of the slots is adapted for releasably receiving the end of the orthodontic wire W to be cinched back. In FIGS. 2A and 2B, as an example, the end of wire W is shown projecting from a conventional orthodontic molar band B mounted on a patient's molar M. As shown in FIGS. 2A and 2B, the angling of the slot allows the orthodontic cinch back instrument to be simply and easily manipulated in order to cinch back the end of wire W. In use, the orthodontist holds the orthodontic cinch back instrument 10 in a manner similar to that of holding a pen or pencil. The distal projection of wire W is inserted into slot 34 (or 35) along the axis of the arch wire W. Slot 34 (or 35) grasps the outer surface of the wire W at a point which gains intimate contact with the distal aspect of the molar band tube. The inner surfaces of the slot 34 (or 35) grasp along the arch wire axis, thereby allow for the production of the required gingival bend at a sharp angle and flush to either the right or left molar band B the of upper and lower arch quadrants (as shown in FIG. 2B).

With reference to FIG. 5, first head 22, and its corresponding slot 34, are preferably dimensioned for engaging a conventional orthodontic wire W. Corresponding to the exemplary dimensions given above, the cylindrical first head 22 may have a height $L_6$ of 3 mm, and outer circular surface 40 may have a diameter of $D_4$ of 2.5 mm. Slot 34, which is dimensioned for securely engaging wire W, may have an exemplary width $L_8$ of 1.0 mm and an exemplary depth $L_7$ of 1.0 mm.

It is to be understood that the orthodontic cinch back instrument is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An orthodontic cinch back instrument, comprising:
   an elongated handle portion extending along a longitudinal axis and having opposed first and second ends;
   first and second shank portions respectively extending longitudinally from the first and second ends of the elongated handle portion;
   first and second arcuate head supports respectively extending from the first and second shank portions, wherein the first and second arcuate head supports are positioned and contoured antisymmetrically with respect to one another about a lateral axis, the lateral axis being orthogonal to the longitudinal axis and bisecting the elongated handle; and
   first and second heads respectively secured to the first and second arcuate head supports, wherein the first and second heads are positioned and angled antisymmetrically with respect to one another about the lateral axis, each of the first and second heads having a slot formed therein adapted for releasably receiving an orthodontic wire to be cinched back, wherein each slot is angled at 45° to the longitudinal axis and has a length of 2.5 mm, a constant width of 1 mm, and a depth of 1 mm.

2. The orthodontic cinch back instrument as recited in claim 1, wherein the first and second shank portions are symmetric with respect to one another about the lateral axis.

3. The orthodontic cinch back instrument as recited in claim 1, wherein the elongated handle portion comprises a central portion extending between the first and second end portions, the central portion being cylindrical and each of the first and second end portions being frusto-conical.

4. The orthodontic cinch back instrument as recited in claim 1, wherein each of the first and second arcuate head supports is substantially S-shaped.

5. The orthodontic cinch back instrument as recited in claim 1, wherein each of the first and second heads is cylindrical.

6. The orthodontic cinch back instrument as recited in claim 5, wherein the slot formed in each of the first and second heads is formed in an outer circular face thereof.

7. The orthodontic cinch back instrument as recited in claim 6, wherein the slot formed in each of the first and second heads is angled with respect to the longitudinal axis.

* * * * *